(12) United States Patent
Vu et al.

(10) Patent No.: US 10,765,461 B2
(45) Date of Patent: Sep. 8, 2020

(54) VARIABLE ANGLE BONE FIXATION DEVICE

(71) Applicant: Depuy Synthes Products, Inc., Raynham, MA (US)

(72) Inventors: Binh Bao Vu, Thorndale, PA (US); George Mikhail, Chester Springs, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 225 days.

(21) Appl. No.: 15/995,924

(22) Filed: Jun. 1, 2018

(65) Prior Publication Data

US 2019/0365436 A1    Dec. 5, 2019

(51) Int. Cl.
*A61B 17/80* (2006.01)
*A61B 17/86* (2006.01)

(52) U.S. Cl.
CPC ...... *A61B 17/8047* (2013.01); *A61B 17/8605* (2013.01); *A61B 17/8004* (2013.01); *A61B 17/8042* (2013.01)

(58) Field of Classification Search
CPC .......... A61B 17/8042; A61B 17/8047
See application file for complete search history.

(56) References Cited

U.S. PATENT DOCUMENTS

| | | | |
|---|---|---|---|
| 2,687,024 A * | 8/1954 | George | F16C 11/0604 464/112 |
| 3,196,463 A * | 7/1965 | Farneth | A61F 2/6607 623/49 |
| 4,936,701 A | 6/1990 | Allen et al. | |
| 5,236,289 A * | 8/1993 | Salyer | B23B 31/08 279/16 |
| 5,807,010 A | 9/1998 | Parker et al. | |
| 6,224,598 B1 | 5/2001 | Jackson | |
| 6,342,055 B1 | 1/2002 | Eisermann et al. | |
| 6,361,535 B2 | 3/2002 | Jackson | |
| 6,767,351 B2 * | 7/2004 | Orbay | A61B 17/68 606/287 |
| 7,166,108 B2 | 1/2007 | Mazda et al. | |
| 7,527,639 B2 * | 5/2009 | Orbay | A61B 17/68 606/287 |

(Continued)

FOREIGN PATENT DOCUMENTS

EP    2 932 927 A1    10/2015

OTHER PUBLICATIONS

"International Search Report", dated Sep. 17, 2019 in connection with International Application No. PCT/IB2019/054156, filed May 20, 2019.

(Continued)

*Primary Examiner* — Zade Coley
(74) *Attorney, Agent, or Firm* — Kramer Amado, P.C.

(57) ABSTRACT

A bone fixation system including a bone fixation element including a head portion having a bore passing therethrough from a first side surface to a second side surface, wherein the bore is perpendicular to a longitudinal axis of the bone fixation element, a securing element positioned within the bore, and a bone plate extending along a plate axis and having a threaded plate hole extending therethrough from a first surface to a second surface configured to contact a bone in an operative configuration.

28 Claims, 8 Drawing Sheets

(56) References Cited

U.S. PATENT DOCUMENTS

| | | | |
|---|---|---|---|
| 7,780,711 B2* | 8/2010 | Orbay | A61B 17/68 606/280 |
| 7,857,839 B2 | 12/2010 | Duong et al. | |
| 8,192,103 B2* | 6/2012 | Tsai | F16D 3/2052 403/114 |
| 9,155,581 B2 | 10/2015 | Asaad et al. | |
| 2002/0143338 A1* | 10/2002 | Orbay | A61B 17/68 606/287 |
| 2004/0260294 A1* | 12/2004 | Orbay | A61B 17/68 606/287 |
| 2008/0177330 A1* | 7/2008 | Ralph | A61B 17/8038 606/290 |
| 2008/0193205 A1* | 8/2008 | Peng | F16C 11/0604 403/114 |
| 2012/0136396 A1 | 5/2012 | Baker et al. | |
| 2013/0060336 A1 | 3/2013 | Hooper et al. | |
| 2015/0354635 A1* | 12/2015 | Mcclymont | B23B 39/14 408/126 |

OTHER PUBLICATIONS

"Written Opinion of the International Searching Authority", dated Sep. 17, 2019 in connection with International Application No. PCT/IB2019/054156, filed May 20, 2019.

* cited by examiner

VARIABLE ANGLE BONE FIXATION DEVICE

TECHNICAL FIELD

Various exemplary embodiments disclosed herein relate generally to a variable angle bone fixation system including a bone fixation element, a securing element and a bone fixation device.

BACKGROUND

Bone fixation plates are often positioned over a fractured or otherwise damaged portion of bone and secured thereto using bone screws inserted through screw holes of the bone fixation plate. The screw holes extend transversely through the bone plate and are sometimes formed with threads to lockingly engage a head of the bone screw. Variable angle screws may be employed which permit a user to insert the screw through the plate at a user-selected angle relative to an axis of the plate hole. However, available variable angle screw systems may produce burrs when the screw head is locked in the plate hole. The burrs mostly arise in systems larger than 3.5 mm and when the screw is angulated relative to the plate hole. In angulated positions, the sharp edges of the plate hole thread act as a die and generate burrs from the screw head thread. Damage to the bone plate or bone screw in this manner is undesirable.

SUMMARY OF EXEMPLARY EMBODIMENTS

A brief summary of various embodiments is presented below. Embodiments address the need to secure a bone plate using a variable angle fixation system.

Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments relate to a bone fixation element including a head portion including a first side surface and a second side surface opposite the first side surface, wherein the first side surface and the second side surface are shaped to allow for variable angle rotation of the bone fixation element, a bore passing through from the first side surface to the second side surface, wherein the bore is perpendicular to a longitudinal axis of the bone fixation element, and a shaft extending along the longitudinal axis of the bone fixation element from a proximal end to a distal end.

Various embodiments relate to a bone fixation system including a bone fixation element including a head portion including a first side surface and a second side surface opposite the first side surface, wherein the first side surface and the second side surface are shaped to allow for variable angle rotation of the bone fixation element, a bore passing through from the first side surface to the second side surface, wherein the bore is perpendicular to a longitudinal axis of the bone fixation element, and a shaft extending along the longitudinal axis of the bone fixation element from a proximal end to a distal end, and a securing element positioned within the bore wherein the bore and securing element are configured to allow for joint-like rotation of the bone fixation element.

Various embodiments relate to a bone fixation system including a bone fixation element including a head portion including a first side surface and a second side surface opposite the first side surface, wherein the first side surface and the second side surface are shaped to allow for variable angle rotation of the bone fixation element, a bore passing through from the first side surface to the second side surface, wherein the bore is perpendicular to a longitudinal axis of the bone fixation element, and a shaft extending along the longitudinal axis of the bone fixation element from a proximal end to a distal end, a securing element positioned within the bore, and a bone plate extending along a plate axis having a threaded plate hole extending therethrough from a top surface to a bottom surface configured to contact a bone in an operative configuration, wherein the bore and securing element are configured to allow for insertion of the bone fixation element at a plurality of angles relative to the bone plate. In various embodiments, the threaded plate hole contains dulled edges. In various embodiments, the plurality of angles includes any angle within a range of 15 degrees relative to an axis normal to the bottom surface of the bone plate.

In various embodiments, the securing element may be a cylindrical pin.

In various embodiments, the first side surface and second side surface of the head portion of the bone fixation element both have a rounded shape.

In various embodiments, the bore includes at least one angled side.

In various embodiments, the system further includes a nut configured to fix the bone fixation element to the bone plate. The nut may include a threaded exterior surface configured to interface with the threaded plate hole. In various embodiments, the head portion of the bone fixation element sits within the nut.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the invention are more fully disclosed in the following specification, reference being had to the accompanying drawings, in which.

Figure 1A:
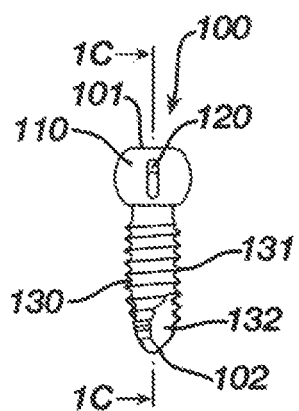
FIGS. 1A and 1B illustrate side views of one embodiment of the bone fixation element.
Figure 1B:
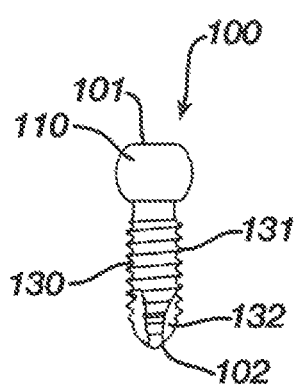

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION OF THE EXEMPLARY EMBODIMENTS

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. The various embodiments described herein are not necessarily mutually exclusive, as some embodiments can be combined with one or more other embodiments to form new embodiments. Additionally, the term, "or," as used herein, refers to a non-exclusive or (i.e., and/or), unless otherwise indicated (e.g., "or else" or "or in the alternative"). Descriptors such as "first," "second," "third," etc., are not meant to limit the order of elements discussed, are used to distinguish one element from the next, and are generally interchangeable. The terms "proximal" and "distal," as used herein, are intended to refer to a direction toward (proximal) and away from (distal) a user of the system.

Embodiments of a bone fixation element 100 and bone fixation system 700 are described below. The bone fixation element 100 may be in the form of a bone screw that is inserted through a bone fixation device 400 to stabilize a fracture or otherwise damaged bone as part of a bone fixation system 700. The bone fixation element 100 includes a screw head 110 that is configured to interact with a drive nut 200, and also includes an elongated shaft 130. The screw head 110 contains a bore 120 that passes through the screw head 110 from a first side surface 111 to a second side surface 112, wherein the bore is perpendicular to a longitudinal axis of the bone fixation element 100. The bore 120 may be configured to have at least one angled side 121. A securing element 300 may be inserted into the bore 120 that passes through the screw head 110 to stabilize the screw head 110 at variable angles in a threaded plate hole 410 of the bone fixation device 400. More specifically, the securing element 300 sits within the bore 120 and allows for variable angle rotation of the bone fixation element 100 within the threaded plate hole 410. The angle of rotation of the bone fixation element 100 with respect to the threaded plate hole 410 may include any angle within a range of 15 degrees relative to an axis normal to the lower surface of the plate.

In some embodiments, the threaded plate hole 410 includes dull edges which prevents the generation of burrs.

FIGS. 1A-1D illustrate a bone fixation element 100. The bone fixation element 100 extends longitudinally from a proximal end 101 including a screw head 110 along an elongated shaft 130 to a distal end 102. In an exemplary embodiment, a first side surface 111 and a second side surface 112 of the screw head 110 are substantially rounded to permit variable angle rotation of the bone fixation element 100, as will be described in greater detail herein. In some embodiments, the top surface of the screw head may be flat. It is noted, however, that the screw head 110 may be formed in any shape that would allow for variable angle insertion of the bone fixation element 100.

Figure 1C:
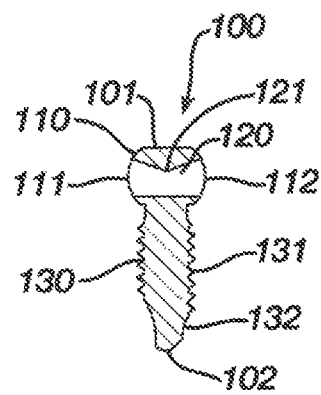
FIG. 1C illustrates a cross-sectional side view of one embodiment of the bone fixation element.
Figure 1D:
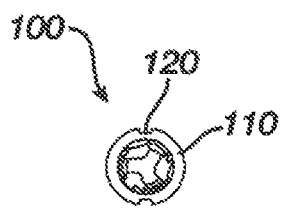
FIG. 1D illustrates a cross-sectional top view of one embodiment of the bone fixation element.
Figure 1E:
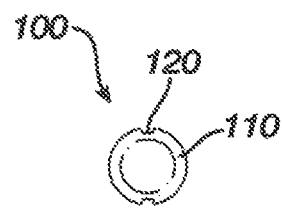
FIG. 1E illustrates a top view of one embodiment of the bone fixation element.

As illustrated in FIG. 1C, the screw head 110 contains a bore 120 that passes through the screw head 110 from a first surface 111 to a second surface 112. The bore 120 may be configured to have at least one angled side 121. In some embodiments, the angled side 121 may include a first slope extending downward from the first surface 111 and a second slope opposite the first slope extending downward from the second surface 112 wherein the two slopes meet at a vertex in the center of the angled side. The two slopes may extend at about a 20 degree angle from the axis of the bore 120 starting at the vertex. In some embodiments, the side of the bore 120 opposite the angled side 121 is flat. In other embodiments, the bore 120 may include a second angled side opposite angled side 121. It is noted that the bore 120 may be formed into any shape that would allow for variable angle insertion of the bone fixation element 100 into the bone fixation system 700. The bore 120 is configured to accommodate a securing element 300 that stabilizes the bone fixation element 100 at a variable angle with respect to a threaded plate hole 410 of a bone fixation device 400.

The elongated shaft 130 is provided with threading 131. The threading 131 of the shaft 130 may be formed with two leads, as those skilled in the art will understand. The multi-lead configuration of the threading 131 aids in linear advancement of the bone fixation element 100 into the bone, as those skilled in the art will understand. As would be understood by those skilled in the art, the length of the shaft 130 is generally selected to conform to requirements of a target procedure. A distal portion of the shaft 130 may comprise one or more notches 132 configured to create a gap in the continuity of the threads 131 and permit self-tapping of the bone fixation element 100, as those skilled in the art will understand. The distal portion of the shaft 130 may taper to a smaller diameter at the distal end 102 to, for example, aid in insertion. The distal end 102 may be sharpened or blunt as desired.

FIGS. 2A-2D illustrate a drive nut 200. The drive nut 200 includes a hollow cylinder 210 having external threads 220 formed into or extending from an exterior surface 211 of the hollow cylinder 210. These threads 220 are adapted to interface with threads formed into or extending from an interior surface 411 of a threaded plate hole 410. The hollow cylinder 210 also includes a top surface 230, opposite a bottom surface 240. The hollow cylinder 210 includes at least one groove on the top surface 230 configured to mate with protrusions on the distal end of a driving tool. In the exemplary embodiment, the hollow cylinder 210 includes grooves 231, 232, 233, 234 configured to permit engagement with a distal end 501 of a driving tool 500.

Figure 2A:
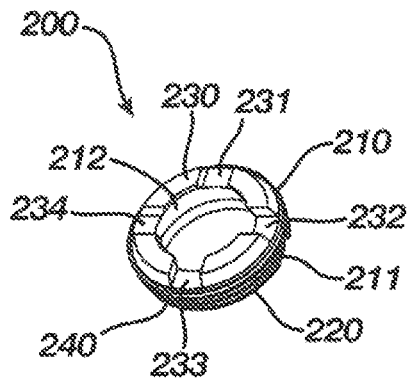
FIG. 2A illustrates a perspective view of one embodiment of a drive nut.
Figure 2B:
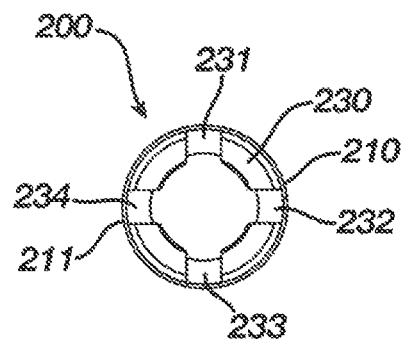
FIG. 2B illustrates a top view of one embodiment of a drive nut.
Figure 2C:
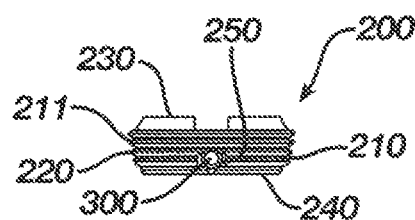
FIG. 2C illustrates a side view of one embodiment of a drive nut.
Figure 2D:
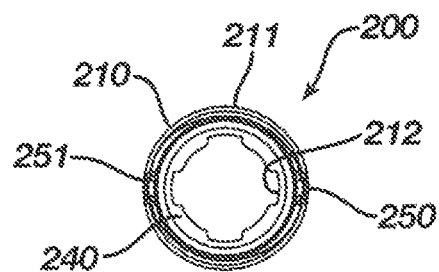
FIG. 2D illustrates a bottom view of one embodiment of a drive nut.

As shown in FIGS. 2C and 2D, the drive nut 200 additionally contains a first bore 250 that extends from the exterior surface 211 to an interior surface 212 of the hollow cylinder 210 and an opposing second bore 251 that extends from the exterior surface 211 of the hollow cylinder 210 to an interior surface 212 of the hollow cylinder 210 opposite the first bore 250. The first bore 250 and second bore 251 are configured to accommodate a securing element 300. The interior surface 212 of the drive nut 200 may be contoured to have a rounded shape to intimately mate with the first side surface 111 and second side surface 112 of the screw head 110. It is noted that the interior surface 212 of the drive nut 200 may be contoured in any other shape that would allow for variable angle insertion of the bone fixation element 100 and locking of the bone fixation element 100.

Figure 3:
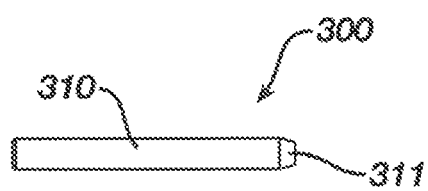
FIG. 3 illustrates a side view of one embodiment of a securing element.

FIG. 3 illustrates a securing element 300. In this embodiment, the securing element 300 is a cylindrical pin. The pin contains an elongated cylinder 310 with a tapered end piece 311. It is noted, however, that the securing element 300 may be formed in any shape that would allow for variable angle insertion of the bone fixation element 100 into the bone fixation system 700. The securing element 300 is configured to be of a sufficient length to extend through bore 120 of the screw head 110 and bores 250, 251 of the drive nut 200 to meet an interior surface 411 of a threaded plate hole 410, shown in FIG. 4A.

Figure 4A:
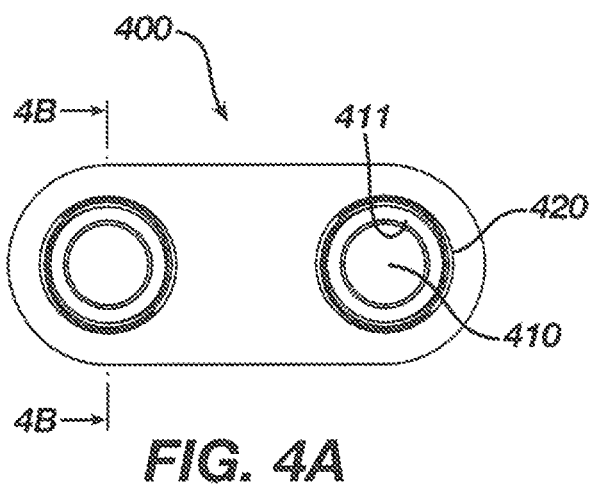
FIG. 4A illustrate a top view of one embodiment of a bone plate.
Figure 4B:
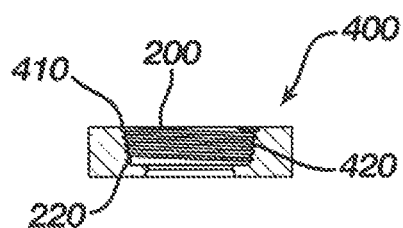
FIG. 4B illustrates a cross-sectional side view of one embodiment of a threaded plate hole.

FIG. 4A illustrates a bone fixation device 400. The bone fixation device 400 may be in the form of a bone plate. The bone fixation device 400 contains at least one plate hole 410, which contains threading 420 extending from the interior surface 411 of the plate hole 410. The threading 420 is configured to interface with the threading 220 on the drive nut 200, as shown in FIG. 4B. The plate hole 410 may be shaped to accommodate variable angle insertion of the bone fixation element 100.

Figure 5A:
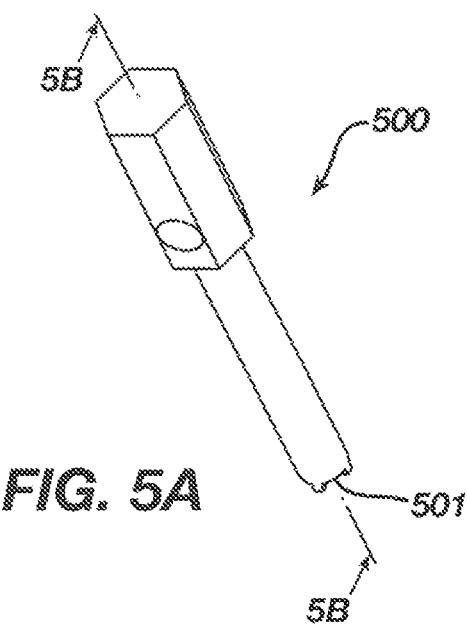
FIGS. 5A and 5B illustrate a perspective and side view, respectively of one embodiment of a drive tool.
Figure 5B:
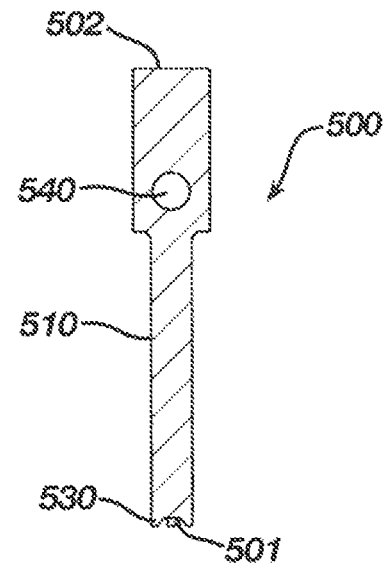

FIGS. 5A-5B illustrates a drive tool 500. The drive tool 500 contains a lower portion 510 at a distal end 501 and an upper portion 520 at a proximal end 502. The lower portion may have a cylindrical shape. The upper portion 520 may have a hexagonal shape. It is noted, however, that the lower portion 510 and upper portion 520 may be formed in any other shape. The distal end 501 of the drive tool 500 may contain at least one protrusion configured to mate with a groove or grooves located on the top surface 230 of the drive nut 200. In the exemplary embodiment, the distal end 501 of the drive tool 500 contains a plurality of protrusions 530 configured to mate with the grooves 231, 232, 233, 234 on the top surface 230 of the drive nut 200.

Figure 5C:
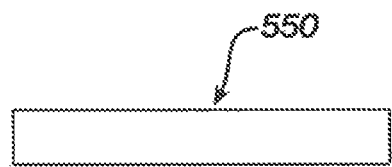
FIG. 5C illustrates a side view of one embodiment of a tool handle used to engage the drive tool shown in FIGS. 5A and 5B.

In the exemplary embodiments of FIGS. 5A and 5B, the width of the upper portion 520 is greater than the diameter of the lower portion 510. The upper portion 520 may contain a through hole 540 configured to accommodate a tool handle 550, which is shown in FIG. 5C. In the exemplary embodiment, the tool handle 550 has a cylindrical shape and is configured to be inserted into the through hole 540 to help provide torque when driving the drive nut 200 and bone fixation element 100 into the bone fixation device 400. It is noted, however, that the through hole 540 and tool handle 550 may be configured in any other shape that would help provide the required amount of torque for driving the drive nut 200 and the bone fixation element 100 into the bone fixation device 400.

Figure 6A:
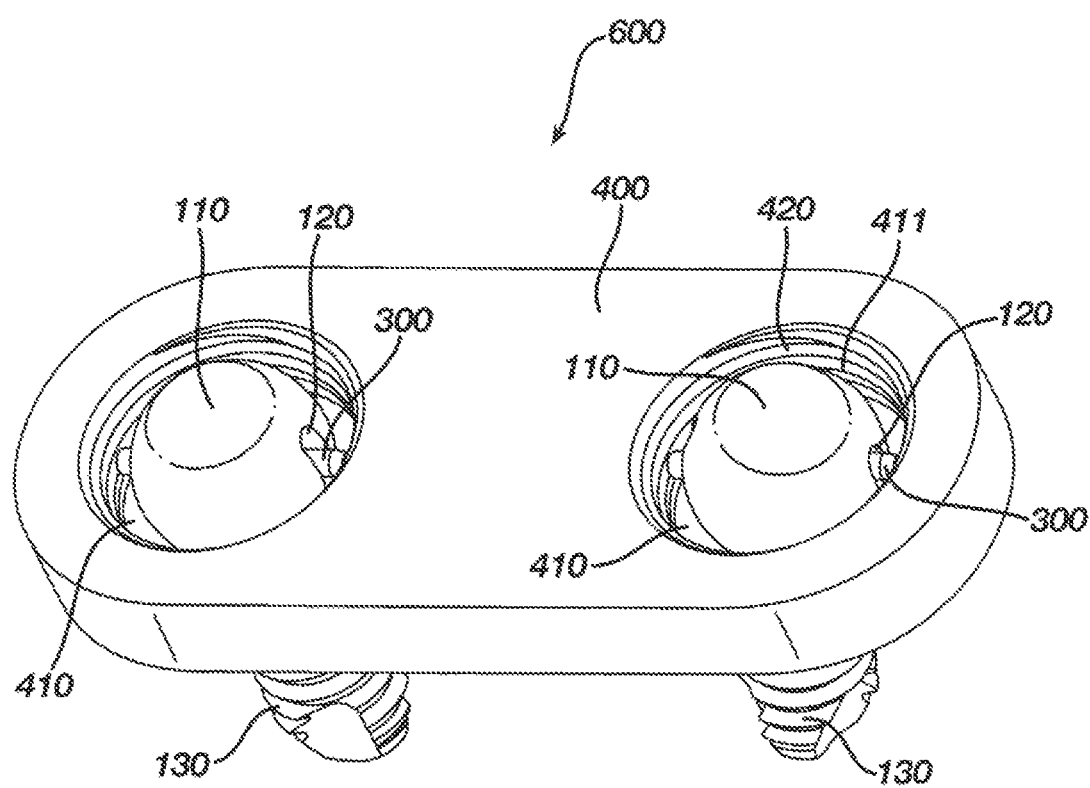
FIG. 6A illustrates a perspective view of one embodiment of the bone plate system.
Figure 6B:
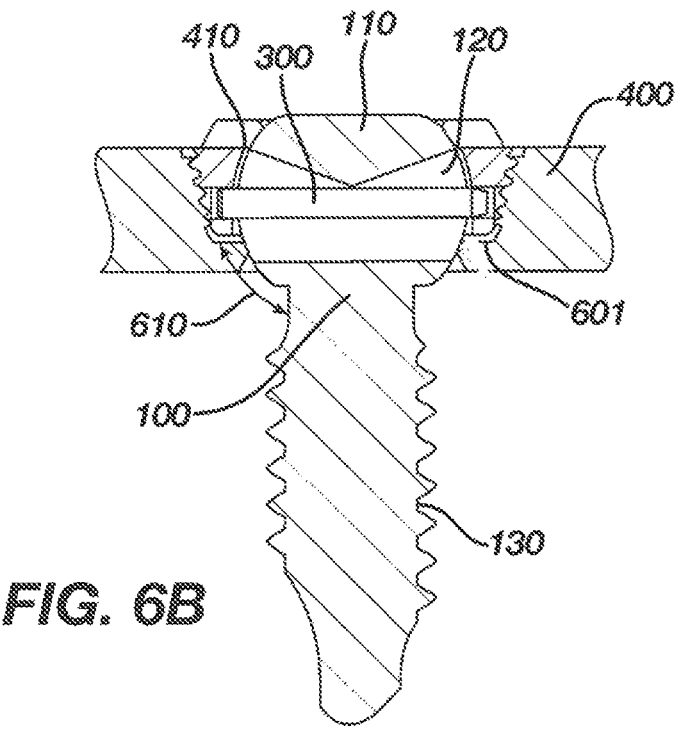
FIGS. 6B and 6C illustrate cross-sectional side views of an embodiment of the bone plate system.
Figure 6C:
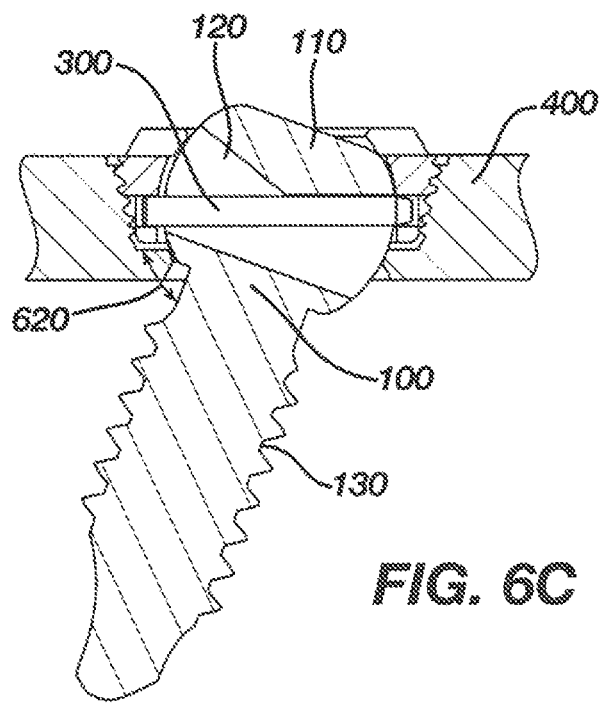

FIGS. 6A-6C illustrate a bone plate system 600 showing the positioning of the securing element 300 within the bore 120 that passes through the spherical screw head 110 of the bone fixation element 100. Also shown is the positioning of the securing element 300 with respect to the interior surface 411 of the threaded plate hole 410 of the bone plate 400. FIGS. 6B and 6C illustrate in more detail the positioning of the securing element 300 within the bore 120 of the bone fixation element 100 at a first angle 610 and a second angle 620.

Figure 7A:
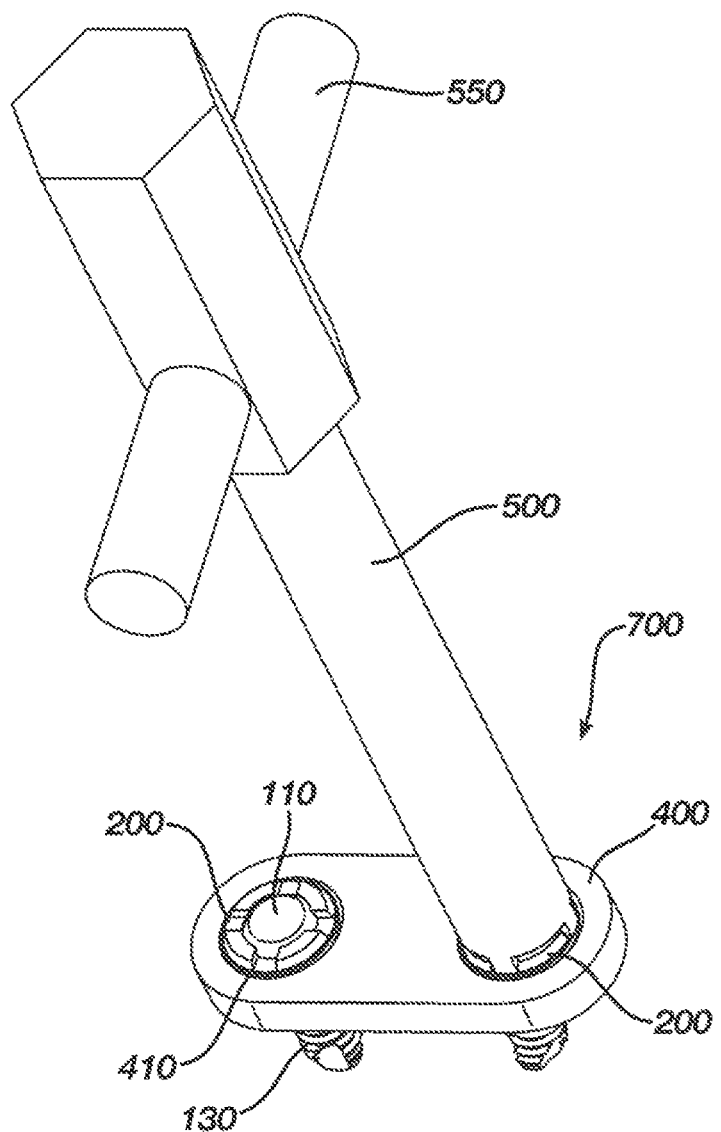
FIG. 7A illustrates a perspective view of another embodiment of the bone plate system.

FIG. 7A illustrates a perspective view of a bone fixation system 700 showing the engagement of the drive nut 200 by the drive tool 500 and tool handle 550. As shown in FIG. 7A, the spherical screw head 110 sits within the drive nut 200. When the drive nut 200 is driven down into the threaded plate hole 410 of the bone fixation device 400 by the drive tool 500, the portion of the drive nut 200 that surrounds the outer surface of the screw head 110 presses down on the screw head 110, as well as the securing element 300 that passes through the screw head 110 and drive nut 200 to secure the bone fixation element 100 at a variable angle in the bone of a patient.

Figure 7B:
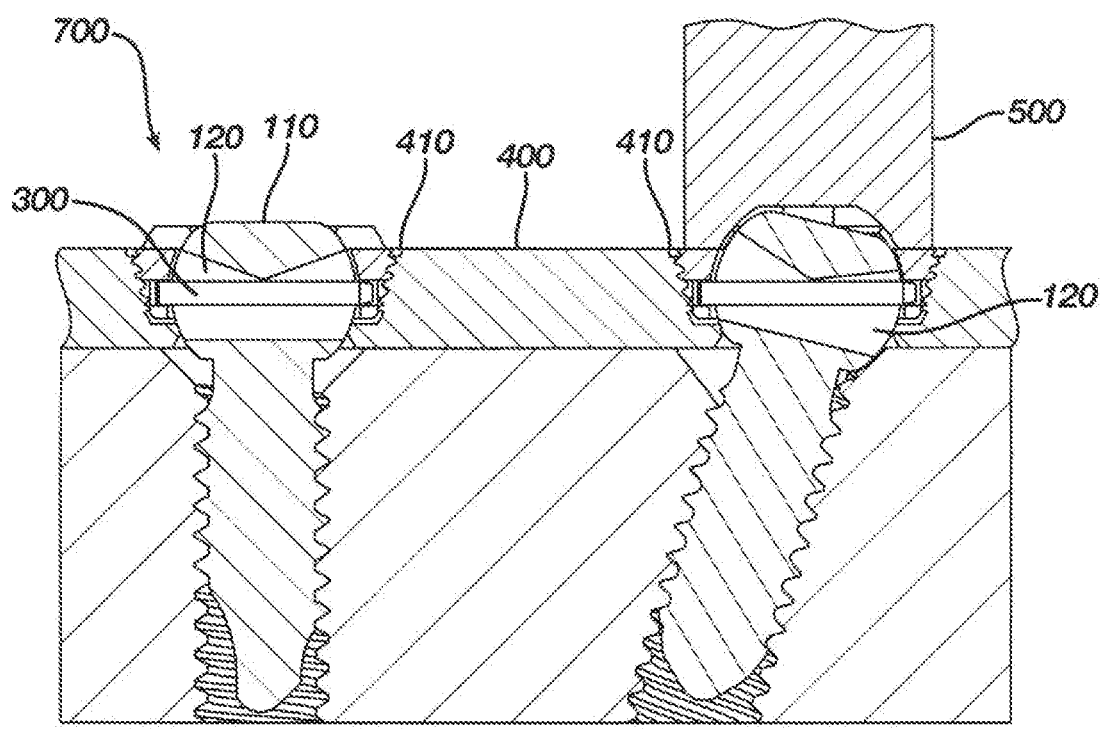
FIG. 7B illustrates a cross-sectional perspective view of another embodiment of the bone plate system.

FIG. 7B illustrates a cross-sectional perspective view of the bone fixation system 700 showing the positioning of the securing element 300 within the bore 120 at variable angles within the threaded plate hole 410 of the bone fixation device 400. As shown in the exemplary embodiment, the securing element 300 remains parallel to the plane of the bone plate 400 and may be positioned to rest completely on a flat side of the bore 120 in a vertical insertion configuration of the bone fixation element 100, or may partially sit against an angled side of the bore 120 in an angled insertion configuration of the bone fixation element 100.

In an operative configuration, the bone fixation element 100 is first coupled with the drive nut 200, and the securing element 300 is inserted through the bores 250, 120, 251. The bone fixation element 100 is then positioned at a desired variable angle and the combination of the bone fixation element, drive nut 200 and securing element 300 are inserted into the threaded plate hole 410. The protrusions on the distal end 501 of the driving tool 500 engage the grooves on the drive nut 200. As the driving tool 500 is turned using the tool handle 550, the threaded exterior surface 211 of the drive nut 200 engages the threads 420 on the plate hole 410. As the drive nut 200 is secured to the threaded plate hole 410, the drive nut 200 presses down on the screw head 110 and securing element 300, fixing the bone fixation element 100 at a desired variable angle. As those skilled in the art will understand, a physician or other user may select a desired angle of insertion to conform to the requirements of a particular procedure. The additional stability provided by the securing element 300 as well as the dulled edges of the threads contained in the threaded plate hole 410 prevents the generation of burrs.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A bone fixation element comprising:
   a shaft extending along a longitudinal axis of the bone fixation element from a proximal portion to a distal portion; and
   a head portion comprising a first side surface and a second side surface opposite the first side surface, wherein the first side surface and the second side surface are shaped to allow for variable angle rotation of the bone fixation element; and
   a bore passing through from the first side surface to the second side surface, wherein the bore is perpendicular to the longitudinal axis of the bone fixation element; and
   a securing element positioned within the bore, wherein the securing element is configured to meet an interior surface of a bone plate hole without penetrating the interior surface of the bone plate hole.

2. The bone fixation element of claim 1, wherein the bore comprises at least one angled side.

3. The bone fixation element of claim 2, wherein the bore comprises two angled sides.

4. The bone fixation element of claim 2, wherein the bore comprises one angled side and one flat side.

5. The bone fixation element of claim 1, wherein the first side surface and the second side surface have a rounded shape.

6. A bone fixation system comprising:
   a bone fixation element comprising:
      a shaft extending along a longitudinal axis of the bone fixation element from a proximal end to a distal end; and
      a head portion comprising: a first side surface and a second side surface opposite the first side surface, wherein the first side surface and the second side surface are shaped to allow for variable angle rotation of the bone fixation element; and
      a bore passing through from the first side surface to the second side surface, wherein the bore is perpendicular to a longitudinal axis of the bone fixation element;
   a securing element positioned within the bore; and
   a hollow cylindrical nut configured to fix the bone fixation element to a bone fixation device:
   wherein the bore and securing element are configured to allow for joint-like rotation of the bone fixation element.

7. The bone fixation system of claim 6, wherein the bore comprises at least one angled side.

8. The bone fixation system of claim 7, wherein the bore comprises two angled sides.

9. The bone fixation system of claim 7, wherein the bore comprises one angled side and one flat side.

10. The bone fixation system of claim 6, wherein the first side surface and the second side surface of the head portion have a rounded shape, and the head portion is configured to be exposed through the hollow cylindrical nut.

11. The bone fixation system of claim 6, wherein the securing element is a pin.

12. The bone fixation system of claim 11, wherein the pin has a cylindrical shape.

13. The bone fixation system of claim 6, further comprising the bone fixation device.

14. The bone fixation system of claim 13, wherein the bone fixation device is a bone plate.

15. The bone fixation system of claim 13, wherein the bore and securing element are configured to allow for variable angle insertion of the bone fixation element into the bone, with respect to the bone fixation device.

16. A bone fixation system comprising:
a bone fixation element comprising:
a shaft extending along a longitudinal axis of the bone fixation element from a proximal end to a distal end; and
a head portion comprising:
a first side surface and a second side surface opposite the first side surface, wherein the first side surface and the second side surface are shaped to allow for variable angle rotation of the bone fixation element; and
a bore passing through from the first side surface to the second side surface, wherein the bore is perpendicular to a longitudinal axis of the bone fixation element; and
a securing element positioned within the bore; and
a bone plate extending along a plate axis and having a threaded plate hole extending therethrough from a top surface to a bottom surface configured to contact a bone in an operative configuration; wherein the bore and securing element are configured to allow for insertion of the bone fixation element at a plurality of angles relative to the bone plate,
wherein the securing element is configured to meet an interior surface of the threaded plate hole without penetrating the interior surface of the threaded plate hole.

17. The bone fixation system of claim 16, wherein the threaded plate hole comprises dulled edges.

18. The bone fixation system of claim 16, wherein the bore includes at least one angled side.

19. The bone fixation system of claim 18, wherein the bore includes two angled sides.

20. The bone fixation system of claim 18, wherein the bore includes one angled side and one flat side.

21. The bone fixation system of claim 16, wherein the first side surface and the second side surface have a rounded shape.

22. The bone fixation system of claim 16, wherein the securing element is a pin.

23. The bone fixation system of claim 22, wherein the pin has a cylindrical shape.

24. The bone fixation system of claim 16, wherein the plurality of angles comprises an angle within a range of 15 degrees relative to an axis normal to the bottom surface of the bone plate.

25. A bone fixation system comprising:
a bone fixation element comprising:
a shaft extending along a longitudinal axis of the bone fixation element from a proximal end to a distal end; and
a head portion comprising:
a first side surface and a second side surface opposite the first side surface, wherein the first side surface and the second side surface are shaped to allow for variable angle rotation of the bone fixation element; and
a bore passing through from the first side surface to the second side surface, wherein the bore is perpendicular to a longitudinal axis of the bone fixation element; and
a securing element positioned within the bore; and
a bone plate extending along a plate axis and having a threaded plate hole extending therethrough from a top surface to a bottom surface configured to contact a bone in an operative configuration; wherein the bore and securing element are configured to allow for insertion of the bone fixation element at a plurality of angles relative to the bone plate; and
a hollow cylindrical nut configured to fix the bone fixation element to the bone plate.

26. The bone fixation system of claim 25, wherein the hollow cylindrical nut comprises a threaded exterior surface configured to interface with the threaded plate hole.

27. The bone fixation system of claim 25, wherein the head portion of the bone fixation element sits within the hollow cylindrical nut.

28. The bone fixation system of claim 25, wherein the hollow cylindrical nut further comprises a first bore that extends from an exterior surface to an interior surface of the nut and an opposing second bore that extends from an exterior surface to an interior surface of the hollow cylindrical nut opposite the first bore, wherein the first bore and second bore are configured to accommodate the securing element.

* * * * *